United States Patent [19]

Barreau et al.

[11] 4,145,423
[45] Mar. 20, 1979

[54] PYRIMIDINYL-1,2-DITHIOLE COMPOUNDS AND ANTI-BILHARZIA COMPOSITIONS THEREOF

[75] Inventors: Michel Barreau; Claude Cotrel, both of Paris; Claude Jeanmart, Brunoy (Essonne), all of France

[73] Assignee: Rhone-Poulenc Industries, Paris, France

[21] Appl. No.: 852,458

[22] Filed: Nov. 17, 1977

Related U.S. Application Data

[62] Division of Ser. No. 766,967, Feb. 9, 1977, Pat. No. 4,104,386.

[30] Foreign Application Priority Data

Feb. 10, 1976 [FR] France .............................. 76 03603
Nov. 30, 1976 [FR] France .............................. 76 36038

[51] Int. Cl.² .................. C07D 239/06; A61K 31/505
[52] U.S. Cl. ..................................... 424/251; 544/242
[58] Field of Search .................. 260/291 R; 424/251; 544/242

[56] References Cited
FOREIGN PATENT DOCUMENTS
1526768 11/1963 France.

OTHER PUBLICATIONS

Böttcher et al., Chem. Ber. vol. 84, pp. 458–463 (1951).
Le Grand et al., Bull. Soc. Chim. (France) pp. 79–83 (1955).
The Chemistry of Heterocyclic Compounds, vol. 21, 1st Part, pp. 382–384 (1966).

Primary Examiner—Nicholas S. Rizzo
Attorney, Agent, or Firm—Stevens, Davis, Miller & Mosher

[57] ABSTRACT

1,2-Dithiole derivatives of the formula:

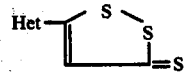

wherein Het represents a pyridazin-3-yl radical, or a pyrimidin-2-yl, -4-yl or -5-yl radical, each such radical being optionally substituted by a halogen atom or by an alkyl radical of 1 through 4 carbon atoms, an alkoxy radical of 1 through 4 carbon atoms, the mercapto radical, an alkylthio radical of 1 through 4 carbon atoms or a dialkylamino group having 1 through 4 carbon atoms in each alkyl radical, are new compounds useful in the treatment of bilharziasis and amoebiasis.

6 Claims, No Drawings

PYRIMIDINYL-1,2-DITHIOLE COMPOUNDS AND ANTI-BILHARZIA COMPOSITIONS THEREOF

This is a division of application Ser. No. 766,967 filed Feb. 9, 1977, now U.S. Pat. No. 4,104,386.

This invention relates to new therapeutically useful derivatives of 1,2-dithiole, to processes for their preparation and pharmaceutical compositions containing them.

The new derivatives of 1,2-dithiole of the present invention are those compounds of the general formula:

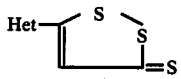

wherein Het represents a pyridazin-3-yl radical, or a pyrimidin-2-yl, -4-yl or -5-yl radical, each such radical being optionally substituted by a halogen atom or by an alkyl radical containing 1 to 4 carbon atoms, an alkoxy radical containing 1 to 4 carbon atoms, a mercapto radical, an alkylthio radical containing 1 to 4 carbon atoms or a dialkylamino group of which each alkyl radical contains 1 to 4 carbon atoms.

According to a feature of the invention, the compounds of general formula I are obtained by the process which comprises reacting phosphorus pentasulphide with a heterocyclic compound of the general formula:

$$\text{Het} - \text{CO} - \text{CH}_2 - \text{COOR} \qquad \text{II}$$

wherein Het is as hereinbefore defined and R represents an alkyl radical containing 1 to 4 carbon atoms.

The reaction is generally carried out in an organic solvent which is inert towards phosphorus pentasulphide, such as pyridine, benzene, toluene, the xylenes or chlorobenzene, at a temperature between 50° and 200° C.

The heterocyclic compounds of general formula II can be obtained by the action of an acetate of the general formula:

$$\text{CH}_3 - \text{COOR} \qquad \text{III}$$

(wherein R is as hereinbefore defined) with a heterocyclic compound of the general formula:

$$\text{Het} - \text{COOR}_1 \qquad \text{IV}$$

wherein Het is as hereinbefore defined and $R_1$ represents an alkyl radical containing 1 to 4 carbon atoms.

The reaction is generally carried out under the usual conditions of the Claisen reaction for the preparation of β-keto-esters. More particularly, the condensation can be carried out at a temperature between 10° and 100° C. in the presence of an alkoxide, for example sodium ethoxide or sodium tert.-butoxide, and optionally in an anhydrous organic solvent such as an aromatic hydrocarbon (benzene, toluene or a xylene), the alcohol formed during the reaction being removed by distillation. It is also possible to effect the condensation by carrying out the reaction in the presence of sodium hydride in diethyl ether.

The heterocyclic compounds of the general formula IV can be obtained by application of the method described by W. S. Leanza et al., J. Amer. Chem. Soc., 75, 4086 (1953), when Het represents a pyridazinyl radical, or by application of the method described by J. L. Wong, J. Org. Chem., 30, 2398 (1965), when Het represents a pyrimidinyl radical.

According to a further feature of the present invention, the compounds of general formula I are obtained by the process which comprises reacting phosphorus pentasulphide with a heterocyclic compound of the general formula:

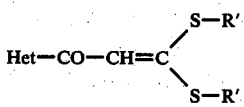

wherein Het is as hereinbefore defined and the symbols R' have the same significance and each represents a hydrogen atom or an alkali metal atom or an alkyl radical containing 1 to 4 carbon atoms, or together form an alkylene radical containing 2 to 4 carbon atoms.

The reaction is generally carried out in a solvent which is inert towards phosphorus pentasulphide (benzene, toluene, a xylene or chlorobenzene) at a temperature between 50° and 200° C.

The heterocyclic compounds of the general formula V wherein the symbols R' each represent an alkali metal atom can be obtained by the action of carbon disulphide, in the presence of an alkali metal alkoxide, on a heterocyclic compound of the general formula:

$$\text{Het} - \text{CO} - \text{CH}_3 \qquad \text{VI}$$

wherein Het is as hereinbefore defined. The reaction is generally carried out in an anhydrous organic solvent, for example benzene or toluene, at a temperature between $-20°$ and $+100°$ C.

The heterocyclic compounds of the general formula V wherein the symbols R' each represent a hydrogen atom can be obtained from a heterocyclic compound of the general formula V, in which the symbols R' each represent an alkali metal atom, by hydrolysis in an acid medium. In general, hydrochloric acid at a temperature of about 20° C. is used for the hydrolysis.

The heterocyclic compounds of general formula V wherein the symbols R' each represent an alkyl radical containing 1 to 4 carbon atoms or together form an alkylene radical containing 2 to 4 carbon atoms can be obtained, when the symbols R' each represent an alkyl radical containing 1 to 4 carbon atoms, by the action of a reactive ester of the general formula:

$$R'' - Z \qquad \text{VII}$$

(wherein R" represents an alkyl radical containing 1 to 4 carbon atoms and Z represents a halogen atom or an ester residue of a sulphuric or sulphonic acid) or, when the symbols R' together form an alkylene radical containing 2 to 4 carbon atoms, by the action of a reactive diester of the general formula:

$$Z - A - Z \qquad \text{VIII}$$

(wherein the symbols Z are as hereinbefore defined and A represents an alkylene radical containing 2 to 4 carbon atoms) on a heterocyclic compound of general formula V wherein the symbols R' each represent an alkali metal atom, which compound can optionally be prepared in situ.

The reaction is generally carried out in an organic solvent such as an alcohol (e.g. methanol) or an aromatic hydrocarbon (e.g. benzene) at a temperature between 20° C. and the boiling point of the reaction mixture.

The compounds of general formula VI can be prepared by applying the method described by Takenari Nakagome and R.N. Castle, J. Het. Chem., 5, 379 (1968), when Het represents a pyridazinyl radical, or in accordance with the method described by M. Robba, Ann. Chim. (Paris), 5, 380–414 (1960) or by F. Zymalkowki and E. Reimann, Arch. Pharm. 299, 362–7 (1966), when Het represents a pyrimidinyl radical.

In the course of the action of phosphorus pentasulphide on a compound of general formula II or on a compound of general formula V, wherein Het represents a pyridazin-3-yl radical or a pyrimidin-2-yl, -4-yl or -5-yl radical each such radical being substituted by an alkoxy radical in the α-position relative to a nitrogen atom, it is possible for a compound of general formula I, wherein Het represents a pyridazin-3-yl radical or a pyrimidin-2-yl, -4-yl or -5-yl radical substituted by a mercapto radical in the α-position relative to a nitrogen atom, to be formed alongside the compound of general formula I wherein Het represents a pyridazin-3-yl or pyrimidin-2-yl, -4-yl or -5-yl radical substituted by an alkoxy radical in the α-position relative to a nitrogen atom.

The new 1,2-dithiole derivatives of general formula I obtained by the aforementioned processes can be purified, if desired, by physical methods such as crystallisation or chromatography.

The 1,2-dithiole derivatives of general formula I exhibit remarkable chemotherapeutic properties. They are particularly useful as anti-bilharzia agents; they are also useful in the treatment of amoebiasis. Furthermore, they have a low toxicity; when administered orally to mice, the 50% lethal dose ($LD_{50}$) is greater than 400 mg/kg animal body weight. Preferably the heterocyclic group attached to the 5-position of the 1,2-dithioles is unsubstituted or is substituted by an alkyl radical containing 1 to 4 carbon atoms, preferably methyl, or by a dialkylamino group containing 1 to 4 carbon atoms in each alkyl radical, preferably dimethylamino. The product of general formula I wherein Het represents the pyridazin-3-yl radical is of very particular interest. Its anti-bilharzia activity manifests itself, in mice infested with *Schistosoma mansoni*, at doses of between 20 and 70 mg/kg animal body weight per day administered orally for 5 days, and at doses of between 10 and 30 mg/kg animal body weight per day administered subcutaneously for 5 days, and in monkeys [*Maccaca mulatta (var. rhesus)*] at doses of about 10 mg/kg animal body weight per day administered orally or subcutaneously for 5 days.

The other compounds of general formula I exhibit the same properties to a lesser degree.

The following non-limitative Examples illustrate the preparation of 1,2-dithiole derivatives of the present invention.

EXAMPLE 1

A suspension of phosphorus pentasulphide (47.2 g) and ethyl 3-(pyridazin-3-yl)-3-oxopropionate (36 g) in toluene (360 cc) is heated for 1 hour at a temperature of about 110° C. After cooling to a temperature of about 40° C., methylene chloride (360 cc) and a saturated aqueous sodium bicarbonate solution (360 cc) are added to the suspension obtained. The solution is stirred for 12 hours at a temperature of about 20° C. and the solid residue is then filtered off. The aqueous phase is decanted and washed with methylene chloride (360 cc). The organic phases are combined, dried over magnesium sulphate, filtered and evaporated to dryness under reduced pressure.

The residue obtained is then dissolved in methylene chloride (50 cc) and the resulting solution is filtered over silica gel (420 g) contained in a column of 5 cm diameter. The column is then eluted with pure methylene chloride (1400 cc). This eluate is discarded. Thereafter the column is eluted with pure methylene chloride (2700 cc). The corresponding eluate is concentrated to dryness under reduced pressure. The solid residue is washed with carbon disulphide (4 × 25 cc) and then with diisopropyl ether (2 × 50 cc). After recrystallisation from 1,2-dichloroethane (800 cc), 5-(pyridazin-3-yl)-1,2-dithiole-3-thione (2.7 g), melting at 250° C., is obtained.

Ethyl 3-(pyridazin-3-yl)-3-oxopropionate can be prepared by adding a solution of ethyl acetate (93.5 g) and of ethyl (pyridazin-3-yl)carboxylate (95.4 g) in anhydrous toluene (200 cc) to a suspension of dry sodium ethoxide (67 g) in anhydrous toluene (350 cc) at a temperature of about 25° C. The reaction mixture is then heated for 18 hours at a temperature of about 90° C. After cooling to a temperature of about 20° C., water (3500 cc) is added to the suspension. The aqueous phase is decanted, washed with diethyl ether (1000 cc) and acidified with concentrated hydrochloric acid (50 cc). The oil which separates out is extracted with methylene chloride (1000 cc), and the aqueous phase is then decanted and washed with methylene chloride (4 × 250 cc). The combined organic phases are dried over anhydrous magnesium sulphate, filtered and evaporated under reduced pressure. Ethyl 3-(pyridazin-3-yl)-3-oxopropionate (86.8 g) is thus obtained in the form of a brown oil.

Ethyl (pyridazin-3-yl)carboxylate can be prepared by the method described by W. J. Laenza, M. J. Becker and E. F. Rogers, J. Am. Chem. Soc., 75, 4086 (1953).

EXAMPLE 2

Ethyl 3-(6-methylpyridazin-3-yl)-3-oxopropionate (1.456 g) dissolved in toluene (9 cc) is added over the course of 8 minutes to a suspension of phosphorus pentasulphide (2.34 g) in toluene (20 cc) heated under reflux. Heating under reflux is continued for 38 minutes. After cooling to a temperature of about 20° C., the insoluble product is filtered off and is then stirred for 30 minutes with a mixture of methylene chloride (50 cc), distilled water (10 cc) and ammonia (d = 0.92; 10 cc). The aqueous phase is separated by decantation and washed with methylene chloride (20 cc). The combined organic phases are washed by decantation with distilled water (10 cc), dried over sodium sulphate, filtered and evaporated to dryness under reduced pressure. The residue obtained is dissolved in methylene chloride (16 cc) and the solution is filtered over silica gel (16 g) contained in a column of 1.6 cm diameter. Elution is carried out with pure methylene chloride (144 cc). This eluate is discarded. Thereafter elution is carried out with pure methylene chloride (48 cc). The corresponding eluate is evaporated to dryness under reduced pressure to give 5-(6-methylpyridazin-3-yl)-1,2-dithiole-3-thione (0.11 g) melting at 242° C.

Ethyl 3-(6-methylpyridazin-3-yl)-3-oxopropionate can be prepared by adding over the course of 5 minutes, at a temperature of about 25° C., a solution of ethyl (6-methylpyridazin-3-yl)carboxylate (5.5 g) in ethyl acetate (29 cc) to a suspension of sodium tert.-butoxide (3.55 g) in anhydrous toluene (60 cc). The reaction mixture is stirred for a further hour at a temperature of about 20° C. and is then poured into distilled water (260 cc). The organic phase is separated by decantation and washed with distilled water (40 cc). The combined aqueous phases are washed with diethyl ether (100 cc), acidified with 4N hydrochloric acid (6 cc) and then extracted with methylene chloride (100 cc, followed by 4 × 50 cc). The combined organic phases are dried over sodium sulphate, filtered and evaporated to dryness under reduced pressure. The residue is stirred with diethyl ether (20 cc). The insoluble material is filtered off and washed with diethyl ether (2 × 5 cc). The combined filtrates are evaporated to dryness under reduced pressure to give ethyl 3-(6-methylpyridazin-3-yl)-3-oxopropionate (0.9 g) melting at 79° C.

Ethyl (6-methylpyridazin-3-yl)carboxylate can be prepared by heating a suspension of (6-methylpyridazin-3-yl)-carboxylic acid (13.8 g) in ethanol (50 cc), together with 1,2-dichloroethane (50 cc) and pure methanesulphonic acid (10.6 g) under reflux for 17 hours. After cooling to a temperature of about 20° C., a 10% (w/v) aqueous sodium carbonate solution (100 cc) is added to the reaction mixture. The aqueous phase is removed by decantation and washed with methylene chloride (3 × 70 cc). The combined organic fractions are washed by decantation with distilled water (30 cc) and dried over sodium sulphate. After filtration and concentration to dryness under reduced pressure, ethyl (6-methylpyridazin-3-yl)carboxylate (14 g) is obtained in the form of a yellow oil.

(6-Methylpyridazin-3-yl)carboxylic acid can be prepared by heating under reflux for 1 hour a solution of 3-cyano-6-methylpyridazine (68.9 g) in a mixture of distilled water (865 cc), 10N aqueous sodium hydroxide solution (290 cc) and ethanol (380 cc). After cooling to a temperature of about 20° C., 12N hydrochloric acid (250 cc) is added to the reaction mixture. After concentration to dryness under reduced pressure, ethanol (1400 cc) is added to the residue obtained and the suspension is stirred for 70 minutes at a temperature of about 20° C. The insoluble product is then filtered off and washed with ethanol (3 × 100 cc). The combined filtrates are evaporated to dryness under reduced pressure to give (6-methylpyridazin-3-yl)carboxylic acid (70 g) melting at 174° C. with decomposition.

3-Cyano-6-methylpyridazine can be prepared in accordance with the method described by Masaru Ogata, Chem. Pharm. Bull., 11, 1511 (1963).

EXAMPLE 3

A suspension of ethyl 3-(6-dimethylaminopyridazin-3-yl)-3-oxopropionate (28 g) and phosphorus pentasulphide (44.4 g) in toluene (590 cc) is heated for 1 hour at a temperature of about 105° C. After cooling to a temperature of about 20° C., the insoluble matter is filtered off and stirred for 1 hour at a temperature of about 20° C. with chloroform (350 cc), ammonia (d = 0.92; 200 cc) and distilled water (200 cc). After filtering off the insoluble matter, the aqueous phase is decanted and washed with chloroform (3 × 100 cc). The combined organic fractions are dried over magnesium sulphate, filtered and evaporated to dryness under reduced pressure. The residue thus obtained is dissolved in methylene chloride (250 cc) and filtered over silica gel (210 g) contained in a column of 3.5 cm diameter. Elution is then carried out with methylene chloride (2000 cc). This eluate is discarded. Finally, elution is carried out with chloroform (1750 cc). The corresponding eluate is evaporated to dryness under reduced pressure. After recrystallisation of the residue from 1,2-dichloroethane (120 cc), 5-(6-dimethylaminopyridazin-3-yl)-1,2-dithiole-3-thione (0.82 g), melting at 272° C., is obtained.

Ethyl 3-(6-dimethylaminopyridazin-3-yl)-3-oxopropionate can be obtained by adding, over the course of 10 minutes at a temparature of about 30° C., a solution of ethyl (6-dimethylaminopyridazin-3-yl)carboxylate (39 g) and of ethyl acetate (35.2 g) in anhydrous toluene (480 cc) to a suspension of sodium tert.-butoxide (38.4 g) in anhydrous toluene (350 cc). The reaction mixture is then stirred for 60 hours at a temperature of about 20° C., after which 12N hydrochloric acid (35 cc) and distilled water (600 cc) are added. The aqueous phase is removed by decantation and washed with methylene chloride (2 × 200 cc). The combined organic fractions are dried over magnesium sulphate, filtered and evaporated to dryness under reduced pressure. Ethyl 3-(6-dimethylaminopyridazin-3-yl)-3-oxopropionate (39.7 g) is thus obtained in the form of a yellow oil.

Ethyl (6-dimethylaminopyridazin-3-yl)carboxylate can be obtained by heating, at a temperature of about 70° C. for 4.5 hours, a suspension of 3-cyano-6-dimethylaminopyridazine (52.7 g) in a mixture of distilled water (600 cc), 10N aqueous sodium hydroxide solution (200 cc) and ethanol (400 cc). After cooling to a temperature of about 20° C., methylene chloride (200 cc) is added to the reaction mixture, which is then left to stand for 12 hours at a temperature of about 20° C. The aqueous phase is removed by decantation, acidified by addition of 12N hydrochloric acid (150 cc) and evaporated to dryness under reduced pressure. Ethanol (360 cc), 1,2-dichloroethane (360 cc) and pure methanesulphonic acid (76 g) are added to the residue thus obtained. The resulting mixture is then heated under reflux for 20 hours. After cooling to a temperature of about 20° C., the insoluble matter which has formed is filtered off and washed with methylene chloride (3 × 20 cc). A saturated aqueous sodium carbonate solution (720 cc) is added to the filtrate thus obtained. The insoluble product which forms is filtered off and washed with methylene chloride (2 × 200 cc). The aqueous phase is removed by decantation and is washed with methylene chloride (2 × 100 cc). The combined organic fractions are dried over magnesium sulphate, filtered and evaporated to dryness under reduced pressure. Ethyl (6-dimethylaminopyridazin-3-yl)carboxylate (50.81 g), melting at 112° C., is thus obtained.

3-Cyano-6-dimethylaminopyridazine can be prepared by heating, at a temperature of about 150° C. for 10 minutes, a suspension of 3-iodo-6-dimethylaminopyridazine (63.7 g) and of cuprous cyanide (34.34 g) in dimethylformamide (380 cc). After cooling to a temperature of about 20° C., the reaction mixture is poured into a mixture of distilled water (3000 cc), methylene chloride (700 cc), ammonium bicarbonate (101 g) and ammonia (d = 0.92; 115 cc). After stirring the mixture for 10 minutes at a temperature of about 20° C., the aqueous phase is removed by decantation and washed with methylene chloride (3 × 300 cc). The combined organic phases are dried over magnesium sulphate, filtered and evaporated to dryness under reduced pressure. 3-Cyano-6-dimethylaminopyridazine (30.5 g), melting at 150° C., is thus obtained.

3-Iodo-6-dimethylaminopyridazine can be prepared by stirring, at a temperature of 20° C. for 48 hours, a solution of 3,6-diiodopyridazine (203.7 g) and of dimethylamine (276 g) in methanol (1500 cc). After evaporation to dryness under reduced pressure, the residue obtained is stirred for 15 minutes with distilled water (1500 cc). The insoluble product is filtered off and washed with distilled water (2 × 200 cc) to give 3-iodo-6-dimethylaminopyridazine (113.7 g) melting at 135° C.

EXAMPLE 4

A solution of ethyl 3-(pyrimidin-4-yl)-3-oxopropionate (55.4 g) in pyridine (100 cc) is added over the course of 2 minutes to a solution of phosphorus pentasulphide (73 g) in pyridine (760 cc) heated to a temperature of about 100° C. Heating of the mixture at a temperature of about 110° C. is continued for one hour. After cooling to a temperature of about 40° C., the reaction mixture is poured into distilled water (8000 cc) containing a filtration adjuvant (75 g). A chestnut-coloured suspension is obtained, which is stirred for 18 hours at a temperature of about 20° C. The insoluble matter is filtered off and washed with distilled water (1500 cc). After drying, the residue obtained is stirred for 2 hours with 1,2-dichloroethane (2500 cc) under reflux. The boiling suspension is filtered and the filtrate is evaporated to dryness under reduced pressure. The residue obtained is dissolved in pure methylene chloride (100 cc) and the resulting solution is filtered over silica gel (70 g) contained in a column of 2.4 cm diameter. Thereafter elution is carried out with pure methylene chloride (700 cc). This eluate is discarded. Elution is then carried out with pure methylene chloride (1000 cc). The resulting eluate is evaporated to dryness under reduced pressure. After recrystallisation from 1,2-dichloroethane (140 cc), 5-(pyrimidin-4-yl)-1,2-dithiole-3-thione (2.3 g), melting at 214° C., is obtained.

Ethyl 3-(pyrimidin-4-yl)-3-oxopropionate can be prepared by adding, over the course of 1 hour at a temperature of about 40° C., a solution of methyl (pyrimidin-4-yl)carboxylate (52 g) and of ethyl acetate (56.5 g) in anhydrous toluene (200 cc) to a suspension of sodium ethoxide (40 g) in anhydrous toluene (200 cc). The reaction mixture is then heated at a temperature of about 80° C. for 7 hours. After cooling to a temperature of about 20° C., water (1700 cc) is added. The aqueous phase is separated by decantation and is acidified to pH5 by addition of 12N hydrochloric acid (28 cc). Crystalline sodium chloride (800 g) is then added, after which the aqueous phase is washed by decantation with methylene chloride (4 × 300 cc). The organic phases are combined, dried over sodium sulphate, filtered and evaporated to dryness under reduced pressure. Ethyl 3-(pyrimidin-4-yl)-3-oxopropionate (55.9 g) is thus obtained in the form of a yellow oil.

Methyl (pyrimidin-4-yl)carboxylate can be prepared in accordance with the method described by J. L. Wong, J. Org. Chem. 30, 2398 (1966).

EXAMPLE 5

A suspension of 3,3-ethylenedithio-1-(6-dimethylaminopyridazin-3-yl)-1-oxoprop-2-ene (2.2 g) in toluene (22 cc) is added over the course of 5 minutes to a suspension of phosphorus pentasulphide (2 g) in toluene (20 cc) heated under reflux. Heating is continued for one hour. After cooling to a temperature of about 20° C., the insoluble product is filtered off and then stirred for 2 hours with a mixture of acetic acid (20 cc), distilled water (20 cc) and chloroform (40 cc). Potassium carbonate (30 g) is then added, after which the aqueous phase is separated by decantation and washed with chloroform (2 × 100 cc). The combined organic phases are dried over sodium sulphate, filtered and evaporated to dryness under reduced pressure. The residue obtained is dissolved in methylene chloride (25 cc) and the solution obtained is filtered over silica gel (30 g) contained in a column of 1.5 cm diameter. Elution is carried out with pure methylene chloride (25 cc). This eluate is discarded. Thereafter elution is carried out with pure methylene chloride (100 cc). The corresponding eluate is evaporated to dryness under reduced pressure to give 5-(6-dimethylaminopyridazin-3-yl)-1,2-dithiole-3-thione (0.05 g) melting at 265° C.

3,3-Ethylenedithio-1-(6-dimethylaminopyridazin-3-yl)-1-oxoprop-2-ene can be prepared by adding, over the course of 20 minutes at a temperature of about 25° C., a mixture of 3-acetyl-6-dimethylaminopyridazine (2.6 g) and of carbon disulphide (1.2 g) in solution in anhydrous toluene (50 cc) to a suspension of sodium tert.-butoxide (3.02 g) in anhydrous toluene (21 cc). Stirring is continued for 10 minutes at a temperature of about 25° C., after which 1,2-dibromoethane (2.95 g) dissolved in anhydrous toluene (15 cc) is added to the reaction mixture over the course of 5 minutes. The reaction mixture is then heated at a temperature of about 102° C. for 5 hours. After cooling to a temperature of about 20° C., the reaction mixture is poured into distilled water (250 cc). The aqueous phase is removed by decantation and is washed with methylene chloride (3 × 100 cc). The combined organic phases are dried over sodium sulphate, filtered and evaporated to dryness under reduced pressure to give 3,3-ethylenedithio-1-(6-dimethylaminopyridazin-3-yl)-1-oxoprop-2-ene (2.5 g) melting at 180° C.

3-Acetyl-6-dimethylaminopyridazine can be prepared by adding, over the course of 20 minutes at a temperature of about 5° C., a suspension of 3-cyano-6-dimethylaminopyridazine (4.44 g) in anhydrous diethyl ether (80 cc) to a solution of methylmagnesium iodide (16.6 g) in anhydrous diethyl ether (90 cc). The reaction mixture is then stirred for 30 minutes at a temperature of about 5° C., after which it is poured into a mixture of distilled water (200 cc), ice (150 g) and ammonium chloride (100 g). The aqueous phase is separated by decantation and is washed with diethyl ether (3 × 50 cc). The combined organic phases are dried over sodium sulphate, filtered and evaporated to dryness under reduced pressure. After recrystallisation of the resulting solid from distilled water (20 cc), 3-acetyl-6-dimethylaminopyridazine (2 g), melting at 130° C., is obtained.

The present invention includes within its scope pharmaceutical compositions which comprise, as active ingredient, at least one 1,2-dithiole derivative of general formula I in association with one or more compatible and pharmaceutically acceptable diluents or adjuvants, and optionally other compatible and physiologically active products. The invention includes especially such preparations made up for oral, parenteral or rectal administration.

Solid compositions for oral administration include tablets, pills, powders, gelatin-coated pills or granules. In such solid compositions the active compound is admixed with at least one inert diluent such as sucrose, lactose or a starch. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

In human therapy the compositions can be used, in particular, in the treatment of bilharziasis and amoebiasis.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. In human therapy the compositions when administered to an adult should generally give doses between 10 mg and 100 mg/kg body weight of active substance per day orally, and between 1 and 25 mg/kg body weight of active substance per day parenterally. In general the physician will decide the posology considered appropriate, taking into account the age and weight and other factors intrinsic to the patient being treated.

The following Examples illustrate pharmaceutical compositions according to the invention.

EXAMPLE 6

Tablets containing 100 mg of active product and having the following composition are prepared in accordance with the usual technique:

| | |
|---|---|
| 5-(pyridazin-3-yl)-1,2-dithiole-3-thione | 100 mg |
| wheat starch | 100 mg |
| precipitated silica | 45 mg |
| magnesium stearate | 5 mg. |

EXAMPLE 7

Tablets containing 200 mg of active product and having the following composition are prepared in accordance with the usual technique:

| | |
|---|---|
| 5-(pyrimidin-4-yl)-1,2-dithiole-3-thione | 100 mg |
| wheat starch | 100 mg |
| precipitated silica | 45 mg |
| magnesium stearate | 5 mg. |

We claim:
1. A 1,2-dithiole compound of the formula:

wherein Het represents a heterocyclic radical selected from pyrimidin-2-yl, pyrimidin-4-yl and pyrimidin-5-yl, or a said heterocyclic radical substituted by a halogen atom or by an alkyl radical of 1 through 4 carbon atoms, an alkoxy radical of 1 through 4 carbon atoms, the mercapto radical, an alkylthio radical of 1 through 4 carbon atoms or a dialkylamino group having 1 through 4 carbon atoms in each alkyl radical.

2. A 1,2-dithiole compound according to claim 1 wherein Het represents pyrimidin-2-yl, pyrimidin-4-yl or pyrimidin-5-yl, or a said heterocyclic radical substituted by a halogen atom, an alkyl radical of 1 through 4 carbon atoms, an alkoxy radical of 1 through 4 carbon atoms, an alkylthio radical of 1 through 4 carbon atoms or a dialkylamino group having 1 through 4 carbon atoms in each alkyl radical.

3. A 1,2-dithiole compound according to claim 1 wherein the heterocyclic group Het is unsubstituted or is substituted by an alkyl radical of 1 through 4 carbon atoms or by a dialkylamino group having 1 through 4 carbon atoms in each alkyl radical.

4. A 1,2-dithiole compound according to claim 1 wherein the heterocyclic group Het is unsubstituted or is substituted by methyl or dimethylamino.

5. The 1,2-dithiole compound according to claim 1 which is 5-(pyrimidin-4-yl)-1,2-dithiole-3-thione.

6. A pharmaceutical composition with anti-bilharzia activity which comprises an effective amount of a 1,2-dithiole compound as claimed in claim 1 in association with one or more compatible and pharmaceutically acceptable diluents or adjuvants.

* * * * *